(12) United States Patent
Mayo et al.

(10) Patent No.: US 6,586,759 B1
(45) Date of Patent: Jul. 1, 2003

(54) METHOD AND APPARATUS FOR ALIGNING AN OPTICAL DETECTING DEVICE

(75) Inventors: Randall David Mayo, Georgetown, KY (US); Herman Anthony Smith, Winchester, KY (US)

(73) Assignee: Lexmark International, Inc., Lexington, KY (US)

( * ) Notice: Subject to any disclaimer, the term of this patent is extended or adjusted under 35 U.S.C. 154(b) by 139 days.

(21) Appl. No.: 09/898,337

(22) Filed: Jul. 3, 2001

(51) Int. Cl.[7] ................................................ G01N 21/86
(52) U.S. Cl. ........................ 250/559.4; 250/556; 347/16
(58) Field of Search .............................. 250/559.4, 556, 250/559.41; 347/16, 14, 19, 105; 356/71, 238.1, 238.2, 239.1, 239.2

(56) References Cited

U.S. PATENT DOCUMENTS

| | | |
|---|---|---|
| 4,617,580 A | 10/1986 | Miyakawa |
| 4,707,138 A | 11/1987 | Coatney |
| 5,139,339 A * | 8/1992 | Courtney et al. ........... 356/446 |
| 5,349,376 A | 9/1994 | Imaizumi et al. |
| 5,592,294 A | 1/1997 | Ota et al. |
| 5,618,120 A | 4/1997 | Ishikawa |
| 5,736,996 A | 4/1998 | Takada et al. |
| 5,754,213 A | 5/1998 | Whritenor |
| 5,764,251 A | 6/1998 | Hashimoto |
| 5,790,143 A | 8/1998 | Takada et al. |
| 5,831,740 A | 11/1998 | Terauchi |
| 6,039,426 A | 3/2000 | Dobbs |
| 6,079,807 A | 6/2000 | Lindstrom et al. |
| 6,084,607 A | 7/2000 | Matsuda |
| 6,164,753 A | 12/2000 | Maza et al. |
| 6,172,690 B1 | 1/2001 | Angulo et al. |
| 6,179,418 B1 | 1/2001 | Mizoguchi et al. |

* cited by examiner

*Primary Examiner*—Que T. Le
(74) *Attorney, Agent, or Firm*—Staas & Halsey; Jacqueline M. Daspit (57) ABSTRACT

A method and apparatus for detecting media type by aligning a media type detector onto a media, with sufficient force, in a media manipulation or sensing apparatus, such that the media type detector will accurately detect a type of media of a media when the media is tilted. A media manipulation or sensing apparatus, where the media type detector is arranged before a picking mechanism, with the media type detector including a force applying mechanism to apply force to a housing sled that is aligned onto the media, and with the housing sled being able to rotate with the media as the media tilts.

30 Claims, 5 Drawing Sheets

METHOD AND APPARATUS FOR ALIGNING AN OPTICAL DETECTING DEVICE

BACKGROUND OF THE INVENTION

1. Field of the Invention

The present invention relates to a method and apparatus for detecting the media type of a media. More particularly, the present invention relates to a method and apparatus for detecting media type by aligning a media type detector onto a media, with sufficient force, in a media manipulation or sensing apparatus.

2. Description of the Related Art

Typically, media manipulation or sensing apparatuses operate in different modes based on the presence of different types of media. A media manipulation or sensing apparatus may operate in a different mode if the media type is of a high glossy type, like a transparency media type, compared to when the media type is of a low glossy type, like plain paper. For example, in a printing environment, certain parameters of printing onto a media are adjusted based upon the media type determination. Typically, in the printing environment, a user must manually indicate to a printing apparatus what type of media is present. Alternatively, some printing systems "pick," or grab, the media and advance it through the printing system, and then determine the type of media, format the parameters for printing thereon, and proceed with printing onto the media. However, these systems are not usually desirable, as the printing system cannot perform the procedure to determine what type of media is being printed on until after advancing the media, which reduces the throughput of media in the printing system. Knowing the media type before picking allows one to adjust certain picking parameters so as to optimize the picking process for that media. This is something that is now done when the user manually indicates to the printing system what type of media is present. Other current media sensors do not provide this ability.

Optical methods and apparatuses previously implemented for such media type detection have included media type detectors having multiple sensors detecting an amount of light reflected off a media. In addition, in one media type detector, as illustrated in FIG. 1, when light source 10 irradiates media 5, light reflecting off media 5 is detected by diffuse sensor 20 and specular sensor 15.

The glossiness of media 5 may then be determined by measuring the ratio of the detected diffuse I(D) and specular I(S) light intensities. Glossier papers tend to reflect specularly more than diffusely, thus a media detecting ratio of I(S)/I(D) can be used to determine the glossiness of media 5, from which the type of media can be determined. Typically, before measuring the media detecting ratio I(S)/I(D), a ratio table is developed, wherein media detecting I(S)/I(D) ratios are stored for a corresponding multitude of different types of media. By referencing back to this ratio table after measuring media detecting ratio I(S)/I(D), corresponding types of media can be differentiated. Typically the determination of a media type according to the media detecting ratio I(S)/I(D) can be accomplished for an overall system in a determining portion by hard wiring or by software in a processing unit.

Figure 1:
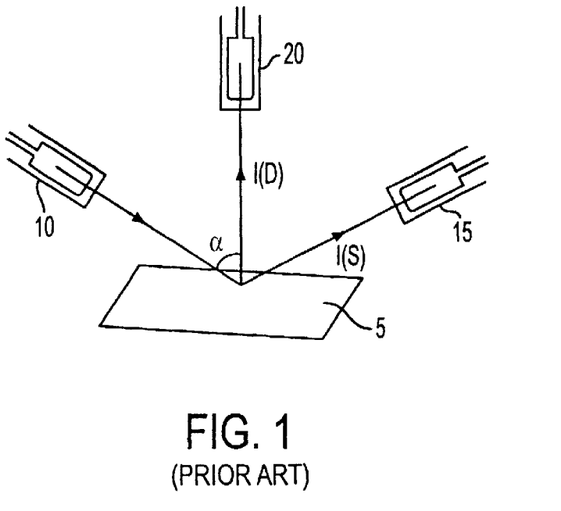
FIG. 1 is an illustration of a media detector having a light source, a diffuse sensor, and a specular sensor.

As illustrated in FIG. 1, diffuse sensor 20 may be arranged at a position normal from media 5, but may be anywhere other than close to an incidence angle a, and specular sensor 15 should be arranged at a position along a clockwise incidence angle a from normal, with light source 10 being arranged at a position along a counterclockwise incidence angle a from normal.

Figure 2A:
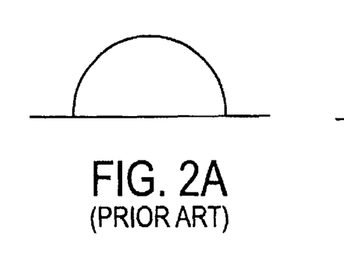
FIGS. 2A–2C are illustrations of light intensity distributions for, respectively, diffuse media, low glossy media, and high glossy media.
Figure 2B:
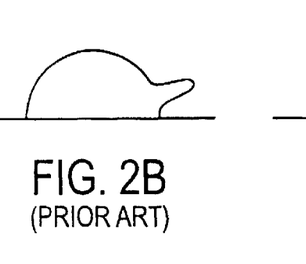
Figure 2C:
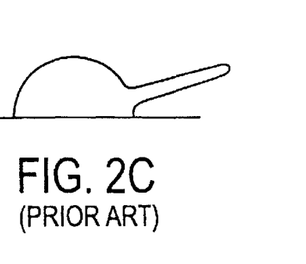

FIGS. 2A–2C illustrate intensity distributions for different types of media. With a perfectly diff-use media type in FIG. 2A, the intensity distribution is substantially equal in all reflected directions. Whereas, with low glossy and high glossy media types shown in FIGS. 2B and 2C, respectively, the intensity in the specular direction is larger than the reflected intensity in non-specular directions.

It is important to keep the light source and the sensors aligned correctly to the media and to minimize any extraneous external light. As noted above with the incidence angle configuration of the light source and specular sensor, a specular light sensor measures the amount of light that reflects off the media at an angle equal to the angle of the radiating light from the light source. When the media is tilted, the measured specular intensity will change since the angle of incidence for the radiating light from the light source has changed. For the specular sensor to detect an accurate specular intensity signal the media should be in a particular position in relation to the light source and specular sensor. As illustrated in FIG. 2C, the specular intensity lobe is very narrow, and if the media is tilted, the specular sensor may not detect an accurate specular intensity as the specular lobe will partially or completely miss the specular sensor. Compared to the specular intensity, the diffuse intensity is not very sensitive to media tilt.

Figure 3A:
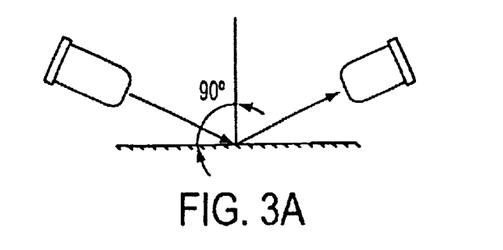
FIGS. 3A–3B are illustrations showing the amount of potential error when the media is not tilted and when the media is tilted, respectively.
Figure 3B:
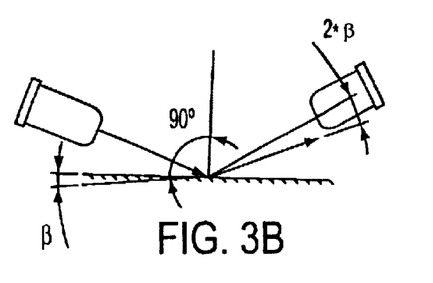

A media tilt can generate a substantial amount of error in the media detecting ratio I(S)/I(D). The amount of error can be such that a media type determination may be incorrect. Therefore, for reliable performance of the media detector, the orientation of the media with respect to the light source and specular sensor is crucial. FIG. 3A illustrates an example where the media is not tilted, resulting in zero error, whereas in FIG. 3B, as the media is tilted relative to the light source and specular sensor, the misalignment angle is twice the tilt angle In a printing system, this tilting of the media can be generated by the influences of static electricity, as well as other factors, on paper in a paper tray. These influences can cause the paper to lift or roll in different areas, and thereby generate the above tilting of the media. Typical media transport systems include conductive materials which generate static electricity. For example, paper passing over a plastic platen will generate a static electric charge. Further, continuing with the paper example, paper stored in a paper tray is usually not held very tightly or may even freely float therein, and therefore, may slide down in the paper tray or may generate a natural curl or waviness with humidity changes. These disclosed problems all detail potential sources of tilting in a media, which must be accounted for to determine media types accurately.

Previous examples of media detectors having an element of alignment include Lowrey, U.S. Pat. No. 1,917,379, where a sensor is applied near a web to detect unevenness, Tajima, U.S. Pat. No. 4,739,605, where a spring loaded reflector is moved by an insertion of media, thereby indicating a presence of media, and in Yoshida et al., U.S. Pat. No. 5,758,982, where an end of a roll of paper is measured by a photosensor being applied against the roll of paper, by a spring system, and by measuring a change in intensity of reflected light to thereby detect an end of the roll of paper. However, none of these references disclose or overcome the aforementioned problems with previous media type detectors.

Therefore, it is necessary to overcome these potential errors by aligning the media detector to compensate for tilting of a media relative to the media detector.

SUMMARY OF THE INVENTION

An object of the present invention is to provide a method and apparatus for detecting the media type of a media by aligning a media detector onto a media, with sufficient force, in a media manipulation or sensing apparatus.

A further object of the present invention is to provide a media manipulation apparatus having a housing sled including at least two light sensors, a force applying mechanism to force the housing sled into contact with a media, and a determining unit to determine a media type of the media based on a ratio of detected light intensities measured by the light sensors while the housing sled is in contact with the media.

Another object of the present invention is to provide a media sensing apparatus having a housing sled including at least two light sensors, a force applying mechanism to force the housing sled into contact with a media, and a determining unit to determine a media type of media based on a ratio of detected light intensities measured by the light sensors while the housing sled is in contact with the media.

A further object of the present invention is to provide a media type detector, for determining a type of media based on a ratio of a detected specular light intensity to a detected diffuse light intensity, including a housing sled including at least a diffuse light sensor and a specular light sensor, and a force applying mechanism to force the housing sled into contact with a media during a detection of the detected specular light intensity and detected diffuse light intensity.

Another object of the present invention is to provide a method of media type detection including applying a media type detector into contact with a media, with the media type detector having a plurality of light intensity sensors, detecting at least two light intensities, and determining a media type of the media by comparing the detected light intensities.

BRIEF DESCRIPTION OF THE DRAWINGS

Advantages of the invention will become apparent and more readily appreciated for the following description of the preferred embodiments, taken in conjunction with the accompanying drawings of which.

DETAILED DESCRIPTION OF THE PREFERRED EMBODIMENTS

Reference will now be made in detail to the preferred embodiments, examples of which are illustrated in the accompanying drawings. In accordance with the preferred embodiments, there is provided a method and apparatus for aligning a media detector onto a media, with sufficient force, in a media manipulation or sensing apparatus to prevent errors in media detecting ratio determinations.

To overcome the aforementioned problems associated with a tilting of a media relative to a light source and specular sensor of a media type detector, a media type detector is aligned onto the media by applying a force to a housing sled riding on the media, with the sled including the light source, diffuse sensor, and specular sensor. In applying a force to a housing sled, riding on a media, several obstacles to good performance must be overcome, including marring of the media by the housing sled, leaving of a residue which could eventually show up after manipulation or sensing of the media, and a potential slowing or stopping of the media during a movement of the media due to the applied force on the housing sled. Of these problems, any movement of the media is a very sensitive process usually, so any potential slowing or stopping of the media during this process is very undesirable. In addition, any stopping or slowing of the media could also generate undesirable skewing upon manipulation of the media, such as printing thereon. Thus, the present invention of applying a pressure to a media sensor on a media has not conventionally been implemented. The present invention compensates for the problems associated with the aforementioned tilting of the media, and overcomes the potential marring and residue depositing by the housing sled, as well as the potential slowing or stopping of the housing sled during movement of the media past the media type detector.

In the printing environment, media moving throughout the system undergoes many different forces. The media is constantly moving under and out of various forces, e.g., when the front edge of a media is driven in a picking device and then passes beyond the picking device, the front edge is typically left free floating with no forces acting thereon. And as some systems have exit picking devices, when the front edge is picked, the media is caused to stretch, which reduces the index accuracy. The use of the aforementioned application of force on the media by the media type detector could also generate similar force problems.

In overcoming the aforementioned problems of different forces being applied to the media, through experimentation and research the following embodiments have been developed. Specifically, by adjusting the applied force of the media detector on the media even while the media is either stationary or moving, these aforementioned problems have been sufficiently eliminated.

Figure 4A:
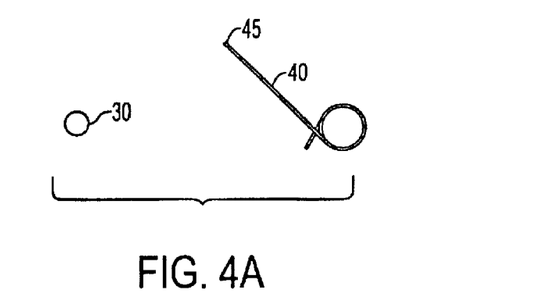
FIGS. 4A–4D are illustrations showing a media detector embodiment, respectively including a torsional spring, a paper insert guide, a housing sled, and a combination of components.
Figure 4B:
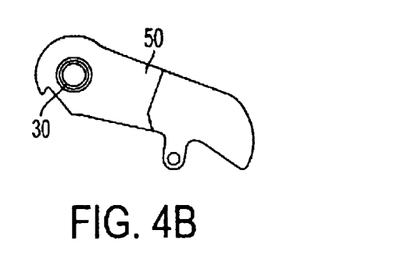
Figures 4C, 4D:
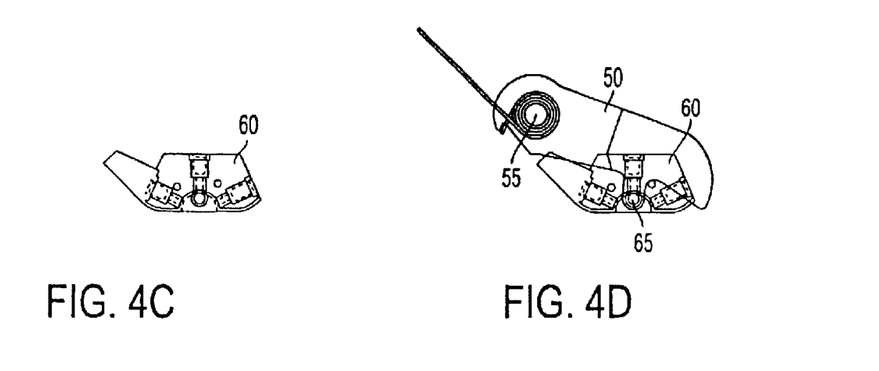

FIGS. 4A–4D illustrate general orientations and components of the present media type detector embodiment. FIG. 4A illustrates the orientation of a torsional spring 40 in relation to a housing rotation shaft 30, with torsional spring 40 having a fixed end 45 that applies a small clamping force to keep a housing sled 60, shown in FIG. 4C, securely seated on a media. FIG. 4B illustrates the orientation of a paper insert guide 50 with housing rotation shaft 30. FIG. 4D further illustrates paper insert guide 50 carrying housing sled 60, indicating a rotation point 55 for paper insert guide 50 and a rotation point 65 for housing sled 60. Because of the force applied by torsional spring 40, paper insert guide 50 and housing sled 60 can rotate with a media as the media is tilting in reference to the light source and specular sensor while being seated on the media. There is sufficient play in paper insert guide 50 and housing sled 60 such that the housing sled may also move laterally small amounts.

As noted above, the force applied by torsional spring 40 must be adjusted based upon the potential types of media that are to be manipulated or sensed in a corresponding apparatus. It was determined that the above indexing problems, resulting from the differing forces being applied to media, can be sufficiently eliminated as the force is reduced. Specifically, as an example in the printing environment, it was determined that an operational range of 20 to 40 grams of force against the media by the media type detector was preferable to eliminate the aforementioned marring, residue depositing, and indexing inaccuracies, noting that both marring and residue depositing were both reduced sufficiently at much higher force levels than 40 grams. At lower force levels below 20 grams the optical accuracy was reduced, and at higher force levels above 40 grams the indexing accuracy degraded. These ranges of forces are only illustrative of the present embodiment, and should not be limited thereto. Different systems, especially media manipulation and sensing apparatuses other than printing apparatuses, will have differing operating ranges based on their individual geometries.

Figure 5A:
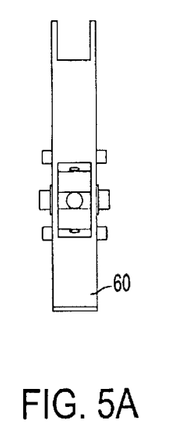
FIGS. 5A–5D are illustrations showing multiple angles of a housing sled, including a bottom view in FIG. 5A, a front view in FIG. 5B, a top view in FIG. 5C, and a section view in FIG. 5D.
Figure 5B:
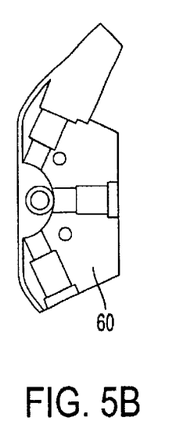
Figure 5C:
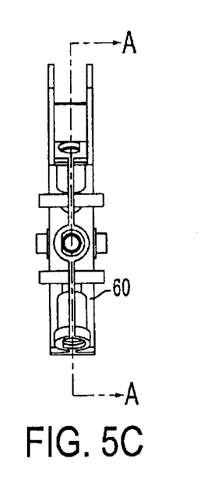
Figure 5D:
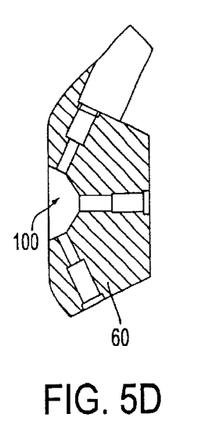

FIGS. 5A–5D illustrate multiple angles of the above housing sled 60 embodiment, including a bottom view in FIG. 5A, a front view in FIG. 5B, and a top view in FIG. 5C. FIG. 5D illustrates a section view along section A—A shown in FIG. 5C. As illustrated in FIG. 5D, a semi-circular cavity 100 has been formed within housing sled 60. Cavity 100 allows sufficient light to be detected by diffuse and specular sensors enclosed within housing sled 60. As the present embodiment determines the type of media based on a media detecting ratio, extraneous external light could alter the media detecting ratio sufficiently that the determined type of media could be inaccurate. These problems have been encountered in conventional systems where there is an air gap between a media detector and a media, where extraneous light can easily make any media type determination unreliable. For example, for some printing systems a media detector can be made practically useless if a cover to the printing system is opened during the media type determination, thereby allowing in extraneous external light. Therefore, the combination of cavity 100 and the alignment of housing sled 60 onto the media surface suppresses the influence of extraneous light.

Figure 6A:
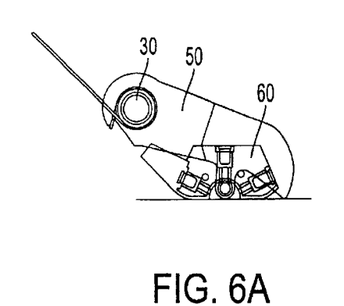
FIGS. 6A and 6B are illustrations showing, respectively, no rotation of a housing sled and tilting of the housing sled when a media is curled.
Figure 6B:
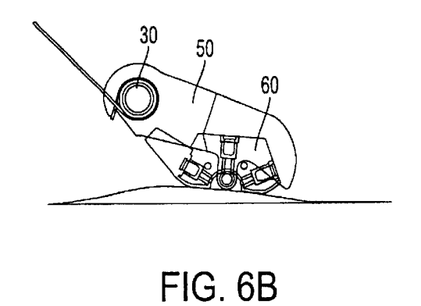
Figure 7A:
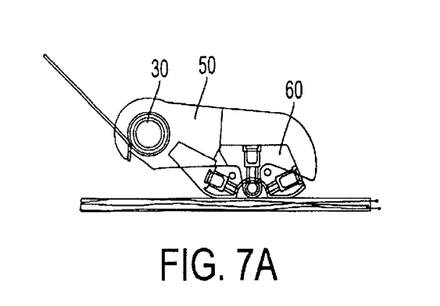
FIGS. 7A and 7B are illustrations showing, respectively, a housing sled seating upon a stack of multiple media sheets, and a single media sheet.
Figure 7B:
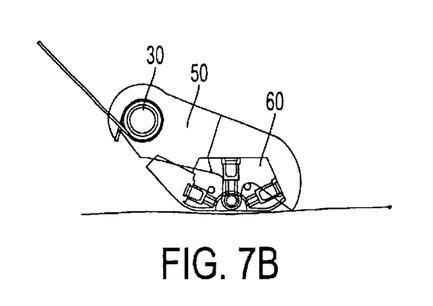

FIGS. 6A and 6B illustrate suppression of the influence of the aforementioned media tilt by housing sled 60 riding on top of the media regardless of whether the media is tilted. FIG. 6A illustrates housing sled 60 on a media without any tilt being presented. Whereas, FIG. 6B illustrates an example where housing sled 60 is seated upon a curled media. Variations in paper shape, height, etc., are compensated for by the rotation of housing sled 60 relative to the paper insert guide 50 and the rotation of paper insert guide 50 relative to housing rotation shaft 30. FIGS. 7A and 7B similarly illustrate this rotation of housing sled 60 and paper insert guide 50 when a stack of media sheets are present, FIG. 7A, and when only a single media sheet is present, FIG. 7B.

Figure 8A:
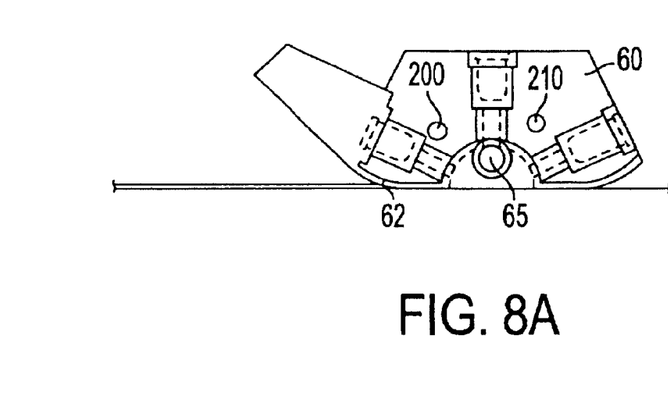
FIGS. 8A and 8B are illustrations showing, respectively, the insertion of a single sheet of media and a stack of multiple media sheets under the media detector.
Figure 8B:
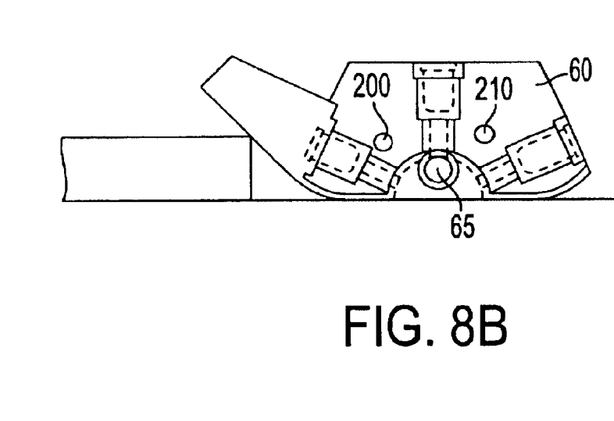

FIGS. 8A and 8B illustrate operation of the present embodiment upon insertion of additional media. As illustrated in FIG. 8A, when one media sheet is inserted into the media detection area of housing sled 60, housing sled 60 contacts the leading edge of the media sheet at contact area 62. Because the corresponding contact area 62 of housing sled 60 has a rounded radius, the single media sheet can slide easily under housing sled 60, even with torsional spring 40 forcing housing sled 60 downward, as a single media sheet is typically less rigid than a stack of papers. The rounded radius of housing sled 60 at contact area 62 minimizes the insertion force necessary for single sheet insertion. Similarly, FIG. 8B illustrates how the angled edge of housing sled 60 will allow for multiple media sheets to be inserted under housing sled 60. As a stack of multiple media sheets are inserted, and contact the edge of housing sled 60, housing sled 60 is rotated about previously described housing rotation shaft 30, thereby allowing housing sled 60 to raise onto the stack of multiple media sheets. To prevent housing sled 60 from rotating too far during paper insertion and removal, rotation limiters 200 and 210 are arranged in housing sled 60 such that they contact the edge of housing sled 60 and limit the amount of rotation. Excessive rotation could allow housing sled 60 to rotate to a point where the bottom of housing sled 60 would not seat correctly on a media sheet after insertion. An example of excessive rotation would be if a large stack of media were to be inserted and housing sled 60 rotated to lay flat on the top of the stack of media. In this case, housing sled 60 would not be able to rotate down to a position on the top of the media stack sufficiently for a media type measurement.

The positioning of a rotation point 65 for the edge of housing sled 60 is also specifically arranged with respect to rotation limiters 200 and 210. By placing rotation point 65 as close to the media transport area as possible, the center of rotation of housing sled 60 is lowered. As housing sled 60 is rotated, an upward force at the point of media contact is countered by a retarding force, the downward force generated at rotation point 65, which generates a twisting moment in the direction opposite of the rotation, forcing housing sled 60 back into a proper downward position for media type detecting. If rotation point 65 were to be higher up away from the media, then when housing sled 60 were to rotate, the upward force at the point of media contact could actually generate a twisting moment in the direction of the rotation and prevent housing sled 60 from properly seating on the media.

The present embodiment has been set forth with torsional spring 40 forcing housing sled 60 into contact with an inserted media. However, additional force generating devices could be utilized as long as sufficient force is generated to keep the light source and sensors aligned with the media. Additionally, the cooperation between paper insert guide 50 and housing sled 60 has been set forth herein, though additional and different devices could be utilized to implement the same or different operations, as long as the principles set forth herein are accomplished, i.e., the light source and media sensors are aligned with the media. Although only diffuse and specular sensors have been set forth herein, the principles disclosed herein are applicable to other types of media detectors, having multiple arrangements and sensors, as long as the media detector is aligned onto the media. The present invention may be placed in several different or even multiple locations within a media manipulating or sensing apparatus.

Figure 9A:
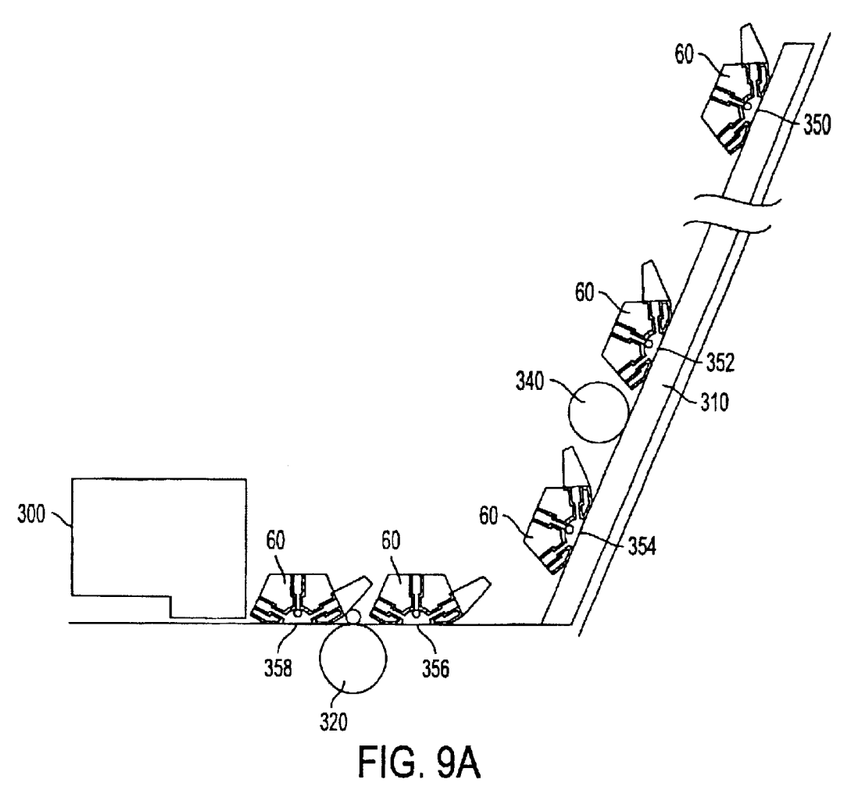
FIGS. 9A and 9B are illustrations showing examples of arrangements of a media detector in a printing environment.
Figure 9B:
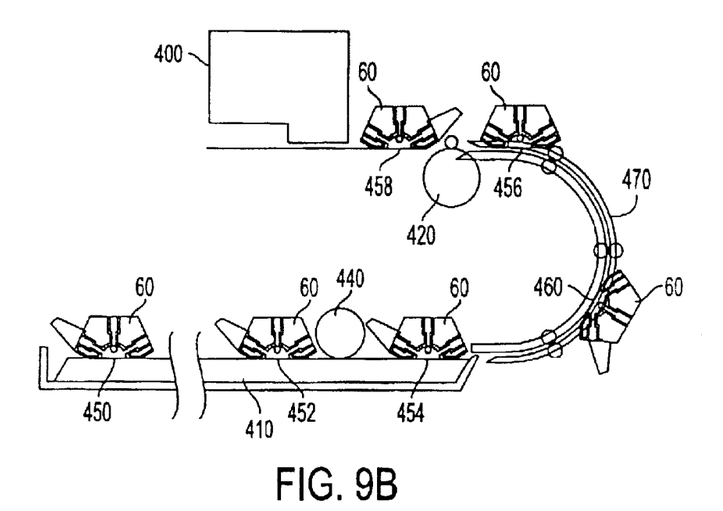

For example, FIGS. 9A and 9B illustrate embodiments where the present invention may be arranged in a printer, for example, in vertical (FIG. 9A) or horizontal (FIG. 9B) sheet feeders.

FIG. 9A illustrates multiple arrangements within a printer for housing sled 60 in a vertical sheet feeder. As illustrated in FIG. 9A, housing sled 60 can be positioned at the trailing edge 350 of paper stack 310, before picking mechanism 340 on paper stack 310 at position 352, after picking mechanism 340 on paper stack 310 at position 354, before feeding nip 320 at position 356, after feeding nip 320 and before printhead 300 at position 358.

FIG. 9B illustrates multiple arrangements within a printer for housing sled 60 in a horizontal sheet feeder. As illustrated in FIG. 9A, housing sled 60 can be positioned at the trailing edge 450 of paper stack 410, before picking mechanism 440 on paper stack 410 at position 452, after picking mechanism 440 on paper stack 410 at position 454, in the paper transport path 470 at position 460, before feeding nip 420 at position 456, after feeding nip 420 and before printhead 400 at position 458. Although these arrangements within a printer have been set forth herein, the present invention should not be limited thereto.

As illustrated in FIGS. 9A and 9B, because the determining of a media type may be performed on a media in media stacks 310 and 410, while a media is being printed upon by printheads 300 or 400, a greater throughput of the printing apparatus may be accomplished. Similarly, picking parameters of picking mechanism 340 and picking mechanism 440 may be adjusted before a picking operation is initiated.

Lastly, the present invention may be employed in multiple types of media manipulation apparatuses, such as photocopiers, printers, media handlers, or any alternative apparatuses which would need a media type detecting device. Media sensing apparatuses could also include several of the aforementioned apparatuses that manipulate the media as well as perform some type of media sensing, such as photocopiers which scan the media and move the media from place to place, as well as apparatuses that perform sensing without any manipulation, such as flat bed scanners, where the type of media may be of importance, but no manipulation is performed on the media. In the sensing apparatuses, similar to the manipulation apparatuses, it is advantageous to perform the media detecting prior to performing the media manipulation or sensing operations. As the present invention detects the type of media, it may also be utilized as a mechanism for detecting the presence of paper.

Thus, although a few preferred embodiments of the present invention have been shown and described, it would be appreciated by those skilled in the art that changes may be made in these embodiments without departing from the principles and spirit of the invention, the scope of which is defined in the claims and their embodiments.

What is claimed is:

1. A media manipulation apparatus, comprising:
   a housing sled including at least two light sensors;
   a force applying mechanism to force the housing sled into contact with a media; and
   a determining unit to determine a media type of the media based on a ratio of detected light intensities measured by the light sensors while the housing sled is in contact with the media.

2. The media manipulation apparatus of claim 1, wherein one of the light sensors is a specular light sensor.

3. The media manipulation apparatus of claim 1, wherein the ratio of detected light intensities includes a ratio of specular light intensity to diffuse light intensity.

4. The media manipulation apparatus of claim 1, wherein the media manipulation apparatus is a printer.

5. The media manipulation apparatus of claim 1, wherein the housing sled is located in a media feeder portion of the media manipulation apparatus before a picking device.

6. The media manipulation apparatus of claim 1, wherein the housing sled includes a first rotation point such that the housing sled rotates the light sensors and a light source in alignment with the media, when the media is tilted.

7. The media manipulation apparatus of claim 6, wherein the housing sled rotates along a second rotation point, with the placement of the second rotation point allowing for a generation of a retarding force countering a rotational force generated by a portion of the media contacting the housing sled.

8. A media sensing apparatus, comprising:
   a housing sled including at least two light sensors;
   a force applying mechanism to force the housing sled into contact with a media; and
   a determining unit to determine a media type of media based on a ratio of detected light intensities measured by the light sensors while the housing sled is in contact with the media.

9. The media sensing apparatus of claim 8, wherein one of the light sensors is a specular light sensor.

10. The media sensing apparatus of claim 9, wherein the ratio of detected light intensities includes a ratio of specular light intensity to diffuse light intensity.

11. The media sensing apparatus of claim 10, wherein the media manipulation apparatus is an optical scanner.

12. The media sensing apparatus of claim 11, wherein the housing sled is located in a media feeder portion of the media sensing apparatus before a picking device.

13. The media sensing apparatus of claim 12, wherein the housing sled includes a first rotation point such that the housing sled rotates the light sensors and a light source in alignment with the media, when the media is tilted.

14. The media sensing apparatus of claim 13, wherein the housing sled rotates along a second rotation point, with the placement of the second rotation point allowing for a generation of a retarding force countering a rotational force generated by a portion of the media contacting the housing sled.

15. A media type detector, for determining a type of media based on a ratio of a detected specular light intensity to a detected diffuse light intensity, comprising:
   a housing sled including at least a diffuse light sensor and a specular light sensor; and
   a force applying mechanism to force the housing sled into contact with a media during a detection of the detected specular light intensity and detected diffuse light intensity.

16. The media type detector of claim 15, wherein the housing sled includes a housing sled rotation point to rotate the housing sled to align with tilted media.

17. The media type detector of claim 16, wherein the housing sled rotation point is positioned in the housing sled in such a manner to allow for a generation of a retarding force countering a rotational force generated by a portion of the media contacting the housing sled.

18. The media type detector of claim 15, wherein the force applying mechanism is a spring.

19. The media type detector of claim 16, further comprising a paper insert guide to carry the housing sled and to apply the force generated by the force applying mechanism to the housing sled, wherein the paper insert guide rotates along a housing rotation shaft to rotate the housing sled to align with tilted media.

20. The media type detector of claim 15, wherein the housing sled includes at least one rounded radius edge minimizing an insertion force necessary for the media to be inserted beneath the housing sled.

21. The media type detector of claim 16, wherein the housing sled includes at least one rotation limiter to limit the rotation of the housing sled.

22. The media type detector of claim 15, wherein the housing sled includes a cavity preventing exterior light from being detected by the diffuse and specular light sensors.

23. A method of media type detection, comprising:

applying a media type detector into contact with a media, with the media type detector having a plurality of light intensity sensors;

detecting at least two light intensities; and determining a media type of the media by comparing the detected light intensities.

24. The method of media type detection of claim 23, wherein the applying of the media type detector includes applying a force to the media type detector before the media is picked by a picking mechanism.

25. The method of media type detection of claim 23, wherein the media type detector is forced into contact with the media by a force between 20 and 40 grams.

26. The method of media type detection of claim 23, wherein the light intensity sensors are contained within a housing that rotates around at least one rotation point such that the housing is in contact with the media and aligns the light intensity sensors with the media when the media tilts.

27. The method of media type detection of claim 26, wherein the rotation point is positioned in the housing in such a manner to allow for a generation of a retarding force countering a rotational force generated by a portion of the media contacting the housing.

28. The method of media type detection of claim 23, wherein the determining of a media type of the media by comparing the detected light intensities includes determining a ratio of specular light intensity to diffuse light intensity.

29. The method of media type detection of claim 23, wherein the determining of a media type is performed on the media while a second media is being printed upon.

30. The method of media type detection of claim 23, wherein picking parameters of a printing apparatus are adjusted, based upon the determining of the media type, and before performing a picking operation.

\* \* \* \* \*